United States Patent
Heide et al.

(10) Patent No.: US 7,087,540 B2
(45) Date of Patent: *Aug. 8, 2006

(54) RESORBABLE BONE REPLACEMENT AND BONE FORMATION MATERIAL

(75) Inventors: Helmut Heide, Kelkheim (DE); Joachim Pabst, Reinheim (DE); Albrecht Dinkelaker, Morfelden-Walldorf (DE); Olaf Pobantz, Wiesbaden (DE)

(73) Assignee: curasan AG, Kleinostheim (DE)

( * ) Notice: Subject to any disclaimer, the term of this patent is extended or adjusted under 35 U.S.C. 154(b) by 369 days.

This patent is subject to a terminal disclaimer.

(21) Appl. No.: 10/085,526

(22) Filed: Feb. 26, 2002

(65) Prior Publication Data

US 2002/0165616 A1   Nov. 7, 2002

Related U.S. Application Data

(63) Continuation-in-part of application No. PCT/EP00/08382, filed on Aug. 28, 2000.

(30) Foreign Application Priority Data

Aug. 26, 1999 (DE) ................................ 199 40 717

(51) Int. Cl.
*C04B 35/447* (2006.01)
*A61F 2/28* (2006.01)

(52) U.S. Cl. ..................... 501/1; 623/23.5; 623/23.56

(58) Field of Classification Search .............. 501/1, 501/80; 623/23.56, 23.5
See application file for complete search history.

(56) References Cited

U.S. PATENT DOCUMENTS

| 4,195,366 A | * | 4/1980 | Jarcho et al. ............ 623/23.56 |
| 5,096,814 A |   | 3/1992 | Aivasidis et al. ............. 435/41 |
| 5,141,510 A |   | 8/1992 | Takagi et al. ........... 301/111.06 |
| 5,531,794 A |   | 7/1996 | Takagi et al. ............ 823/23.56 |
| 6,340,648 B1 |   | 1/2002 | Imura et al. .................. 501/80 |
| 6,383,519 B1 |   | 5/2002 | Sapieszko et al. |
| 6,511,510 B1 |   | 1/2003 | de Bruijn et al. ........ 623/23.56 |
| 6,521,246 B1 |   | 2/2003 | Sapieszko et al. |
| 2003/0049328 A1 | * | 3/2003 | Dalal et al. ................. 424/602 |
| 2003/0171822 A1 | * | 9/2003 | Lo .......................... 623/23.56 |
| 2004/0019385 A1 | * | 1/2004 | Ayers et al. ............... 623/23.5 |
| 2004/0064194 A1 |   | 4/2004 | Irie et al. ................. 623/23.61 |

FOREIGN PATENT DOCUMENTS

| DE | 3123460 A |   | 2/1982 |
| DE | 3810803   | * | 10/1989 |
| DE | 3810803 A |   | 10/1989 |
| JP | 1-108143  | * | 4/1989 |

OTHER PUBLICATIONS

DeGroot, Ph.D., Klaas (Editor); "Bioceramics of Calcium Phosphate", *CRC Press, Inc.*, Boca Raton, Florida (1983).
Meachim, G., Brooke G. and Pedley, R.B., "The tissue response to acrylic particles Implanted in animal muscle"; *Biomaterials 1982*, vol. 3 Oct.; pp. 213-219.

(Continued)

*Primary Examiner*—Karl Group
(74) *Attorney, Agent, or Firm*—Myers Bigel Sibley & Sajovec PA

(57) ABSTRACT

The invention relates to a resorbable bone replacement and bone formation material (augmentation material) based on porous β-tricalcium phosphate (β-TCP).

28 Claims, 6 Drawing Sheets a)

b)

OTHER PUBLICATIONS

Sjoholm, Ingvar and Edman, Peter; "Acrylic Microspheres In Vivo. I. Distribution and Elimination of Polyacrylamide Microparticles after Intravenous and Intraperitoneal Injection in Mouse and Rat", *The Journal of Pharmacology and Experimental Therapeutics*, vol. 211, No. 3 (1979), pp. 656-662.

Klawitter, J.J., Bagwell, J.G., Weinstein, A.M. Sauer, B.W.; "An Evaluation of Bone Growth into Porous High Density Polyethylene", *J. Biomed. Mater. Res.*, vol. 10 (1976), pp. 311-323.

DeGroot et al., *Die klinische anwendbarkeit von Calciumphosphat-Keramiken*, Zahnarztliche Mitteilungen Heft 18/65. 75, Jahrgang (1985, pp. 1938-1940.

Roempp Chemie-Lexikon ed. 7 (1975, Franckhsche Verlagsbuchhaltung Stuttgart.

Koster, K. Helde H. Konig R., Histologische Untersuchungen an der Grenzflache zwischen Knochengewebe und Calciumphosphat-, Calciumaluminat- und Aluminiumoxidkeramik, Z. Orthop. 115 (1977), pp. 693-699.

Erbe et al., *Comparison of Vitoss and Pro Osteon 500R in a Canine Model at 1 Year*, 47th Annual Meeting, Orthopaedic Research Society (Feb. 25-28, 2001), p. 0975.

510(k) *Summary Vitoss™ Scaffold Synthetic Cancellous Bone Void Filler*, Summary of S&E, Vitoss Scaffold, Orthovita. Inc. (Dec. 14, 2000) pp. H1-H3.

Letter from Dept. of Health & Human Services re: *Vitoss™ Scaffold Synthetic Cancellous Bone Void Filler* (Dec. 14, 2000), 2 pages.

Indications for Use Statement, *Vitoss™ Scaffold Synthetic Cancellous Bone Void Filler*, Vitoss Scaffold 510(k) Notification (Dec. 7, 2000) 1 page.

510(k) *Summary* (Nov. 26, 2002) 2 pages.

Galols et al. *Use of β-tricalcium phosphate in foot and ankle surgery: a report of 20 cases*, Blackwell Science Ltd., Foot and Ankle Surgery Dec. 2001 7:217-227.

*Filling of Bone Defects with Tricalcium Phosphate Beta in Traumatology*, In Ann Chir Dec.; 2000 125(10):972-81 (concise statement).

PCT International Search Report, International Application No. PCT/EP 00/ 08382 filed Aug. 28, 2000.

\* cited by examiner

Fig. 4a Batch I 174 after the first synthesis baking. A residual reflection of hydroxyapatite (arrow) is clearly discernible. The red lines denote β-TCP.

Fig. 4b X-ray powder diffraction diagram of batch I 174 after grinding, compaction and repeat baking. Unreacted starting material was not added. The reflection of hydroxyapatite (arrow) has not changed in relation to the reflections of β-TCP.

Fig. 5a Batch K 286 after the first synthesis baking. A hydroxyapatite reflection (arrow) is discernible.

Fig. 5b Batch K 286 after comminution, addition of unreacted starting material and second synthesis baking. Hydroxyapatite is no longer discernible.

ured in phase-pure form. In
the case of materials corresponding to the prior art, that
requirement is clearly not met. (G. Bauer and G. Hohn-
berger: Ursachen unterschiedlichen Verhaltens von bioak-
tiven Calcium Phosphatkeramiken im Organismus [Causes
of differing behaviour of bioactive calcium phosphate
ceramics in the body]. cfi (Ber. d. DKG) 66 (1989), 23–27)

RESORBABLE BONE REPLACEMENT AND BONE FORMATION MATERIAL

CROSS-REFERENCE TO RELATED APPLICATIONS

This application is a continuation-in-part of International Application No. PCT/EP00/08382, filed Aug. 28, 2000, now WO 01/13970 A1 published Mar. 1, 2001, and claims priority benefits of German application DE 19940717.7 filed Aug. 26, 1999.

PRIOR ART a) Phase purity

Since the sixties, calcium orthophosphates, especially α- and β-tricalcium phosphate (TCP) and also hydroxyapatite (HAP) have been investigated and used as so-called bioactive and resorbable bone replacement materials. A comprehensive materials science and biomedical literature exists on the subject, in which respect, by way of example, reference may here be made to the comprehensive summary by K. deGroot: Bioceramics of Calciumphosphates. K. deGroot (Editor) CRC Press, Bota Raton, Fla. 1983, 1. The good biocompatibility of that group of materials is understandable considering the extensive chemical similarity of those materials to the inorganic constituent of bone, hydroxyapatite. The scientific discoveries from the period of pioneering research into that group of materials are adequately described by the work referred to above. Accordingly, the good compatibility with bone, the more or less pronounced resorbability and the so-called "bioactivity" are reported, bioactivity being understood to mean the positive chemical interaction of those calcium phosphates with living bone, which finds expression in the formation of a direct bond, without connective tissue, with the bone. The precise links between the materials characteristics and the biological properties of those materials have not, as yet, been clarified in many regards and it is only in recent times that discoveries have been made in respect of the correlation between the materials science, thermodynamic and crystallographic characteristics of those materials and the biological reactions of bone.

In the case of foreign-body reactions of bone it is generally assumed that particles less than 20 micrometers in size are taken up and transported away or metabolised (phagocytosis) by macrophages (phagocytes). Those processes are discussed, inter alia, in the following publications: Meachim et al. in Biomaterials, 3 (4) (1982) 213–219 and Sioholm et al. in J. Pharmacol. Exp. Ther., 211 (3) (1979) 656–662.

In a further study, deGroot reports (DeGroot et al.: Die klinische Anwendbarkeit von Calciumphosphat Keramiken [The clinical applicability of calcium phosphate ceramics]. Z. M.Fortbildung 75, 1985, 1938–1940) on the particulate breakdown of TCP into phagocytosable sub-particles which can pass into the lymphatic system. According to findings on which the invention is based, those phenomena have something to do with the phase make-up, phase purity and structure of the TCP material investigated therein. Accordingly, the two most important forms of TCP, α- and β-TCP, despite their chemical similarity, have different solubilities and, especially, different conversion characteristics in the biological environment. In many TCP materials, the two forms of tricalcium phosphate are present together, with phases of lesser stability (lattice energy and solubility) being concentrated at the particle boundaries. When heterogeneous materials of that kind are subjected to continuing chemical dissolution and biological degradation processes, such a material will break down in the manner described by De Groot. Because of the concentration of "foreign phases" at the particle boundaries of the principal constituents of the material, that breakdown process mechanism is active even when there are very small amounts of phase impurities. From that it follows that such resorbable implant materials must be very carefully synthesised in phase-pure form. In the case of materials corresponding to the prior art, that requirement is clearly not met. (G. Bauer and G. Hohnberger: Ursachen unterschiedlichen Verhaltens von bioaktiven Calcium Phosphatkeramiken im Organismus [Causes of differing behaviour of bioactive calcium phosphate ceramics in the body]. cfi (Ber. d. DKG) 66 (1989), 23–27)

b) Porosity

Microporosity

Microporosity is understood to mean that porosity of a ceramic material which is no longer discernible to the naked eye, that is to say pore radii that are approximately ≦20 micro-meters (Römpp Chemie Lexikon [Römpp Chemistry Dictionary], 7th Edition (1975), Franckh'sche Verlagshandlung, Stuttgart).

In addition to the phase purity, the nature of the pore structure of a resorbable bone replacement material is an important factor.

To begin with, it should first be stated that increasing the porosity of the structure increases the specific surface area and also, as a result, the resorbability. At the same time, the mechanical strength decreases and the tendency to particulate breakdown increases. In spite of that basic relationship, the prior art attempts to achieve a resorption rate that is as high as possible by providing the internal surface of the material with particle-to-particle binding that is as weak as possible by using or "cultivating" constituents of the structure that are as finely particulate as possible. As expected, biomaterials according to the prior art that are "cultivated" for high resorption rates are mechanically so imperfect that they generally come into consideration only for applications in which no appreciable mechanical demands are made. The uncontrollable breakdown into microscopically fine sub-particles results, moreover, in increased formation of poly-nuclear giant cells, which has to be regarded as an unfavourable cellular reaction to the biomaterial in question. Rapid implant resorption occurring synchronously with restoration of newly formed bone, without the occurrence of any appreciable breakdown of the structure, is desirable.

According to the prior art, relatively large, formed, monolithic pieces made from such microporous materials are also used as implants for bridging relatively large bone defects. In the case of such formation materials, in which only microporous material structures are present, it is found that, after superficial resorption, pronounced stagnation of the resorption process takes place after a short time and, later, rejection processes may even occur. According to findings on which the invention is based, those phenomena are in no way to be attributed to the chemical material properties of the calcium phosphates in question but, rather, are based on the following negative effect: The microporosity of those materials actually has a capillary suction effect on fluids in the region surrounding the implant. As a result, those fluids are drawn into the interior of the implant materials, where they remain for relatively long periods while newly formed bone grows around the external regions of the implant. Bone structures and blood vessels are not able to penetrate into the internal regions and the diffusion distances are too large for a diffusive exchange of substances. Accordingly, in the interior of such "inaccessible" regions of monolithic implant materials, necrosis of the body fluids and cells previously drawn in by the capillary action may occur.

Macroporosity

According to Römpp Chemie Lexikon [Römpp Chemistry Dictionary], 7th Edition (1975), Franckh'sche Verlagshandlung, Stuttgart, macroporosity is understood to refer to pore radii $\geq 20$ micrometers.

From as early as the seventies the possibility has been investigated of using calcium phosphate implant materials which have an open, interconnected macroporosity (K. Köster, H. Heide and R. König: Histologische Untersuchungen an der Grenzfläche zwischen Knochengewebe und Calciumphosphatkeramik etc. [Histological investigations at the boundary surface between bone tissue and calcium phosphate ceramic etc.], Z. Orthop. 115, (1977), 693–699) in order to make it possible for bone to penetrate as quickly as possible.

That aspect is a feature of many products corresponding to the prior art. However, macroporous products of that kind corresponding to the prior art have serious disadvantages, which shall be discussed below:

one of the current methods for producing a macroporous structure consists of adding porosity-imparting agents, which are introduced, for example, in the form of foams or spherical plastics, which give rise to spherical pores on solidification of a hydraulically setting starting compound or on ceramic baking.

That porosity-imparting method has the disadvantage that the pores are predominantly closed. They are accordingly not available for penetration by budding-in bone and, in the end, result only in lowering of the strength of the implant region.

A similar effect is produced by porosity-imparting methods carried out in many different ways by burning out irregularly shaped organic "spacer materials". In ceramics technology, sawdust, for example, is conventionally used. In that method and in numerous similar porosity-imparting media, irregularly distributed pore shapes and sizes are formed—which can be described as statistical porosity—which are used in ceramics technology for reducing the weight of the materials concerned and for improving thermal insulation. Statistical porosities of that kind are also used, based on those methods, in biomaterials according to the prior art. They are, however, completely unsuitable for the purpose, for the following reasons: Statistical porosities contain a wide spread of pore radius distribution, as well as, especially, numerous closed pores and pore tracks having "dead ends", which are unsuitable for homogeneous and complete penetration by bone.

Building on that finding, a further kind of pore structure, obtained from biogenic products, is also currently in use. One such pore structure is so-called spongy bone, for example from cattle bone, which for the purpose of being used as implant material, is conditioned by more or less complete removal of protein constituents. Also used are the porous structures of corals and certain algae in order to obtain pore structures which, in view of their biogenic formation, are apparently optimal. Apart from the chemically questionable properties of such substances (for example, undefined chemical compositions and immunological problems in the case of cattle bone etc., as well as chemical activities that are entirely different to that of bone in the case of the use of algae and corals), there are also reasons of principle why such pore structures cannot be considered especially suitable: To begin with, it may first be stated that although the mentioned pore structures, as end products of a cybernetic modification process, have formed optimally modified systems in the original organisms in question, those systems no longer bear any relation to the biomechanical demands in the implant site. (In such a biomaterial, bone can necessarily only form in the open pore spaces, which in the original organism were holes or, in other words, were not biofunctional loading zones. At best, therefore, the "negative" of a functional bone structure can be formed.) Even disregarding such relatively "philosophical" reasons, the basic arguments against "statistical porosities" also argue against such structures: In the case of such biogenic pore structures, ingrowing bone structures are also impeded, for example, as a result of pores that are too small, or the osteons budding in are prevented, by numerous changes in direction, from achieving a biofunctional, lamellar orientation as quickly as possible, actually causing the formation of "woven bone", which grows in unordered fashion.

The invention accordingly relates to a resorbable bone replacement and bone formation material (augmentation material) based on porous β-tricalcium phosphate (β-TCP).

In the case of the formation material according to the invention, the macropores, seen in themselves, can contribute approximately 35% to the overall porosity (that is to say, microporosity+macroporosity) of the material. In spite of the high overall porosity of more than 50%, the strength of this implant material, compared to a statistical porosity of the same order of magnitude, is still sufficiently high for formed implant pieces still to be very readily handled. Without doubt, however, the strengths are so low here that functional strengths of the implant sites cannot be achieved without additional mechanical supporting devices, such as, for example, an external fixation or the known screw arrangements with plates etc. in many cases immediately after implantation. One of the crucial advantages of the formation material according to the invention is, however, that cross-linking of the implant structure with functionally oriented and spatially cross-linked bone structures takes place very rapidly so that, compared to other implant materials corresponding to the prior art, very rapid restoration of the functional loadability of the implant zone is achieved. Consequently, the naturally low strength of calcium phosphate materials is compensated solely by the macroporous structure according to the invention. Even during the penetration phase of such structures, the osteons that bud in, which are already matched in their functional orientation to the loading situation, quickly supply the entire implant region with vessels and, consequently, ensure rapid resorption of the formation material according to the invention, with—simultaneously—a biofunctionally loadable state being very quickly achieved. The bone replacement and formation material according to the invention meets the general requirement for restoration of the implant site as quickly as possible solely by means of the described features with respect to phase purity microporosity and function-matched macroporosity in ideal manner. Those positive factors can be further enhanced by combining the implant materials according to the invention with growth-promoting constituents of the patient's blood, the so-called platelet rich plasma or so-called bone morphogenic proteins. That can be accomplished, for example, by soaking the micro- and macroporous spaces of the implant materials, immediately before the operation, with preparations, in liquid form, of the growth-promoting media.

Further aspects of the solution to the technical problems and advantages of the bone replacement and formation material according to the invention are set out hereinbelow.

The invention further relates to a formation material characterised in that the chemical and crystalline purity, the fabric structure, the microporosity and the macroporosity of the augmentation material make possible rapid, foreign-body-reaction-free, biochemically orientated integration and resorption in bone.

Furthermore, the formation material according to the invention can be characterised in that at least 99.5% of the material consists of pure β-tricalcium phosphate (β-TCP).

Furthermore, the formation material according to the invention can be produced by baking β-tricalcium phosphate (β-TCP) at least twice and especially at least three times and preventing the formation of thermodynamically stable adjacent phases of β-TCP.

Furthermore, the formation material according to the invention can be produced by
(i) baking a phosphate powder of a chemical composition the residue on baking of which yields theoretically chemically pure tricalcium phosphate as a sintered-together presynthesis product, and powdering that presynthesis product,
(ii) optionally baking the powdered presynthesis product together with phosphate powder according to step (i) and powdering the material obtained and optionally repeating step (ii) once or more than once,
(iii) compressing the powdered product obtained in step (i) or step (ii) together with phosphate powder according to step (i) to form blanks and subjecting the blanks formed to final ceramic baking and
(iv) providing the compressed or baked blanks with tubular pores.

Furthermore, the formation material according to the invention can be produced by
(i) starting from a presynthesis product obtainable by baking a phosphate powder of a chemical composition the residue on baking of which yields theoretically chemically pure tricalcium phosphate as a sintered-together presynthesis product, and powdering that presynthesis product,
(ii) optionally baking the powdered presynthesis product together with phosphate powder according to step (i) and powdering the material obtained and optionally repeating step (ii) once or more than once,
(iii) compressing the powdered product obtained in step (i) or step (ii) together with phosphate powder according to step (i) to form blanks and subjecting the blanks formed to final ceramic baking and
(iv) providing the compressed or baked blanks with tubular pores.

Furthermore, the formation material according to the invention can be obtainable by baking at a temperature below 1200° C. in the β-tricalcium phosphate (β-TCP) phase region.

Furthermore, the formation material according to the invention can be obtainable by using in step (ii) and/or step (iii) from 1 to 50% by weight, especially from 1 to 25% by weight, phosphate powder (based on the total weight of phosphate powder and already baked material).

Furthermore, the formation material according to the invention can be characterised in that the sintered structure has a uniform, interconnected microporosity with pore widths in the region of from 2 to 15 μm and especially from 4 to 10 μm and/or the matrix of the augmentation material is tightly sintered to microporosity, especially with microparticles that are loosely incorporated in the sintered structure and/or phagocytosable, having a diameter of max. 15 μm, being absent.

Very advantageous cellular reactions are found if the bone replacement material has the structural parameters according to the invention: As a result of the production route, which shall be discussed hereinbelow, the material according to the invention is distinguished by an open, interconnecting microporosity having pore widths of from 2 to 15 μm. The ceramic matrix itself constitutes a network of tight structural elements firmly sintered to one another, in which loosely incorporated sub-particles, which could be dissolved out by cell activities, are absent.

Furthermore, the formation material according to the invention can be characterised by a microporosity of 20% by volume or more, preferably from 20 to 40% by volume, and especially 30% by volume or more, of the overall porosity (consisting of micro- and macro-porosity).

Figure 1:
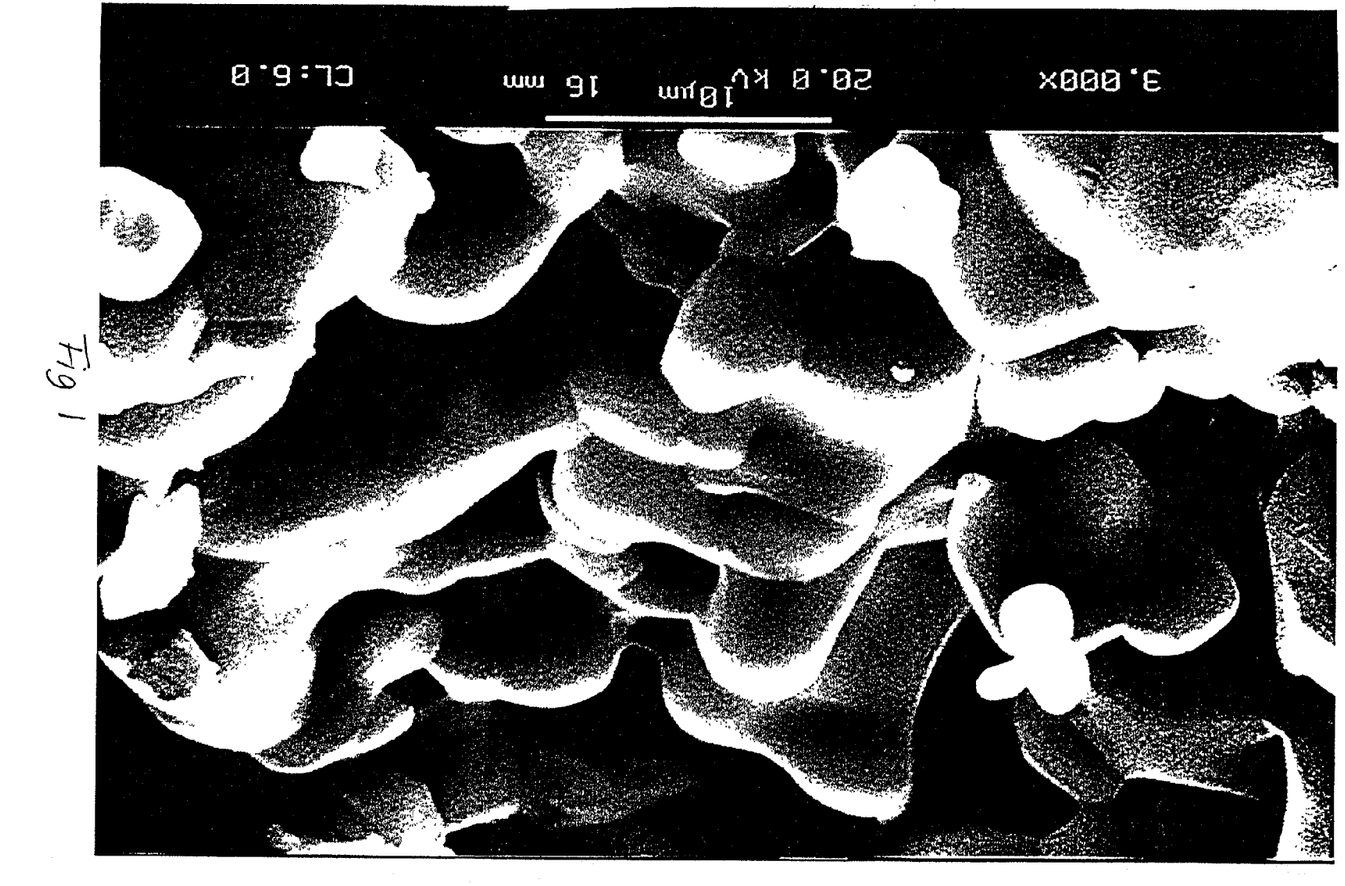
FIG. 1 shows the micro-structure of an augmentation material according to the invention.
Figure 2:
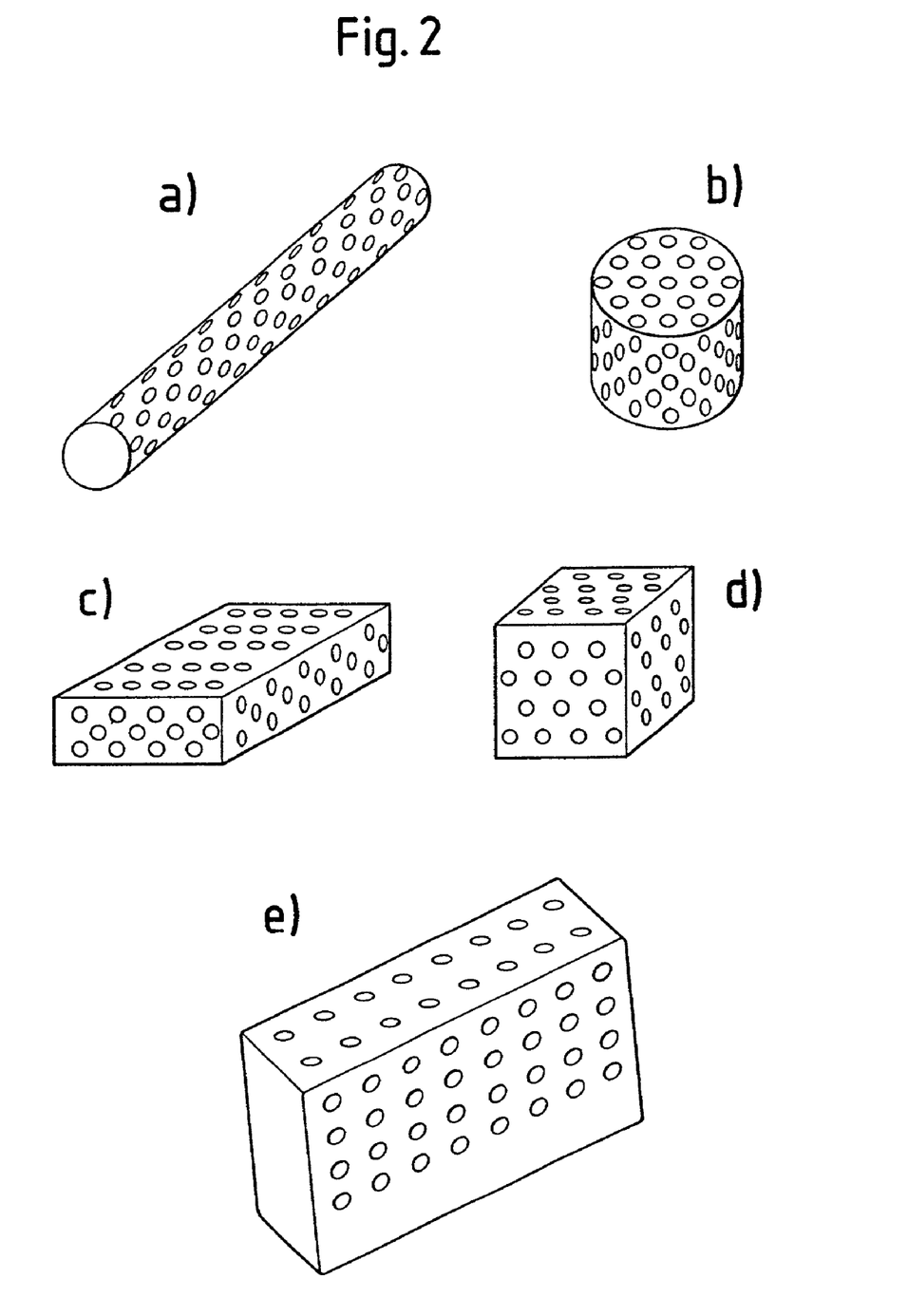
FIGS. 2a to 2e show examples of augmentation articles according to the invention in the form of semi-finished products.

Also characteristic of the micro-structure according to the invention are the rounded surfaces of the fabric-forming structural elements (cf. FIG. 1), which relate especially advantageously to the living cells in the implant site, because mechanically induced irritation of the site tissue is largely avoided as a result. Those rounded fabric elements also cause stress and strain in the materials science sense to be minimised so that the materials according to the invention have optimum mechanical strength despite their comparatively high microporosity of more than 30% by volume.

Furthermore, the formation material according to the invention can be obtainable by providing the compressed blank with tubular pores with the aid of a compression mould of optionally more than one part.

Furthermore, the formation material according to the invention can be obtainable by providing the baked blank with tubular pores by means of milling or drilling.

Furthermore, the formation material according to the invention can be characterised in that the formation material is in block form, with 2- or 3-dimensionally oriented macroscopic tubular pores passing through each block, which are in each case arranged perpendicular to the block surface or to an imaginary plane laid through the block or against the block and form an interconnecting system of tubular pores.

Furthermore, the formation material according to the invention can be characterised in that a block intended for implantation, together with its tubular pores, can be so oriented for implantation or on processing prior to implantation that at least one direction of orientation of the tubular pores corresponds to a biomechanically or biofunctionally intended direction of growth.

Furthermore, the formation material according to the invention can be characterised by tubular pores that have radii in the region of from 100 to 2000 μm and especially from 500 to 2000 μm.

In contrast to the prior art, the bone replacement and formation material according to the invention is provided with a very regularly oriented tubular porosity which, with radii of preferably from 500 to 2000 μm, has optimum size characteristics for the budding-in of osteons. Such pores of parallel arrangement pass through the materials according to the invention in at least two, in certain applications even three, tubular systems arranged perpendicular to one another. For optimum matching to the functional task, one of the tube orientations on implantation should be in accordance with the main direction of growth of the adjacent host bone. Because the pore systems arranged perpendicular to one another in the implant materials according to the invention interconnect in all planes, the bone structures that bud in cross-link very quickly to form a well vascularised spatial network of load-bearing bone structures. As a result, the bone formation material according to the invention constitutes, in the truest sense of the term, an optimum guide rail system.

That accords with studies by Klawitter et al.; (Klawitter, J. J. et al.: An Evaluation of Bone Growth into Porous High Density PE. J.Biomed.Res.10:311, 1976), according to which the smallest functional building elements of bone, the osteons, which are tube-like structures having complete supply organs for maintaining vital functions, can only grow into pore tracks that have a pore width of at least 100 μm. Smaller pore systems do not permit biofunctional penetration by living bone. From that it follows that biomaterials having statistical pore systems, for example those corresponding to the current prior art, cannot be a satisfactory solution.

Furthermore, the formation material according to the invention can be characterised in that the formation material, present in block form, is penetrated by the tubular pores spaced apart at a defined spacing with respect to one another, especially at a spacing that corresponds to a wall thickness of not more than from 1500 to 4000 μm and especially from 2000 to 3000 μm.

According to further investigations upon which the invention is based, the critical material thicknesses in the case of monolithic material structures having solely microporosity are above 3–4 mm. If the wall thickness is lower, the body fluids can be exchanged with the surrounding living tissue by means of diffusive processes so that necrotic processes do not take place.

The requirement arrived at above in the section "Microporosity" for wall thicknesses of not more than from 3 to 4 mm is met in the defined macroporous material according to the invention by means of the fact that the tubular pores are set so closely together that the material thicknesses are at no point greater than about 3 mm.

Furthermore, the formation material according to the invention can be characterised by an overall porosity (consisting of micro- and macro-porosity) of more than 50% by volume.

Furthermore, the formation material according to the invention can be characterised by a macroporosity of from 25 to 50% by volume, and especially from 30 to 40% by volume, of the overall porosity (consisting of micro- and macro-porosity).

Furthermore, the formation material according to the invention can be characterised in that the block form is a simple geometric shape, especially that of a cube, cuboid, taper, cone or disc.

Furthermore, the formation material according to the invention can be characterised in that it is a semi-finished product, especially for subsequent mechanical processing, preferably for individual adaptation in the case of a bone defect in mouth or jaw medicine, orthopaedic surgery or trauma surgery.

Furthermore, the formation material according to the invention can be characterised in that the material is compressed, especially baked or sintered, only to a degree such that it can be processed using tools available to the practitioner, especially using a rasp, file, scalpel or a dentist's instrument.

Furthermore, the formation material according to the invention can be characterised in that it has been brought into the form of an individual prosthesis with the aid of a medical CAD/CAM method.

The invention is illustrated in further detail hereinafter by means of figures and implementation examples, wherein.

EXAMPLES

1. According to an advantageous embodiment, the ceramic implant material according to the invention can be synthesised from the two inorganic materials calcium hydrogen phosphate and calcium carbonate from stoichiometric mixtures by sintering according to the formula $$2CaHPO_4 + CaCO_3 \xrightarrow{+ \text{ temp.}} \beta\text{-}3CaO \cdot P_2O_5 + CO_2 \uparrow + H_2O \uparrow$$

The synthesis is carried out at temperatures below 1200° C. in the β-TCP phase region. In order to avoid the formation of undesirable subsidiary phases such as that of α-TCP, of amorphous phases and of hydroxyapatite, rectification of the material is carried out by sintering several times in the above-mentioned temperature range.

2. Forming of the implant material according to the invention is advantageously carried out by compressing the phase-pure TCP powder to form long cylindrical blanks, baking these at T<1200° C. and bringing the blanks obtained in that matter into the desired form by means of chip-removing methods (milling, turning and drilling).

3. Manipulable implants can be produced, according to an advantageous embodiment, from the bone replacement material according to the invention, in the form of rod-shaped cylindrical, cuboidal or cube-shaped and other semi-finished products which can be brought into the desired shaped using suitable tools (files, rasps, saws etc.) (cf. FIG. 2). Those semi-finished products can be produced by customary compressing techniques from powders but also by pouring techniques of the kind that Is customary in ceramics.

The tubular porosity according to the invention is produced by drilling and milling after ceramic baking of those shaped articles.

Figure 3:
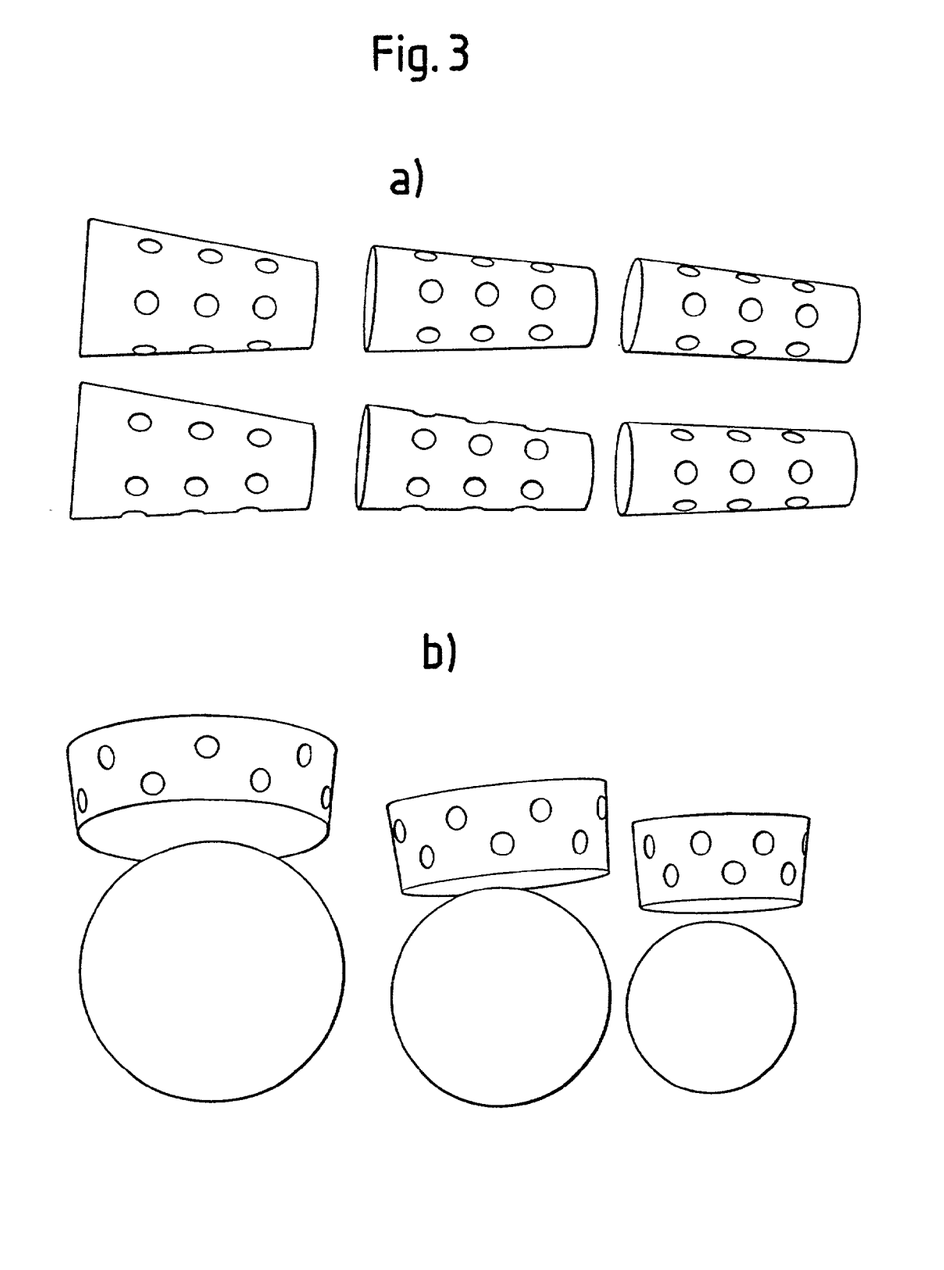
FIG. 3a shows an alveolar augmentation article according to the invention.
FIG. 3b shows an augmentation article according to the invention for a trephination closure.
FIG. 3c shows an augmentation article according to the invention in the form of a sinus lift.
Figure 3C:
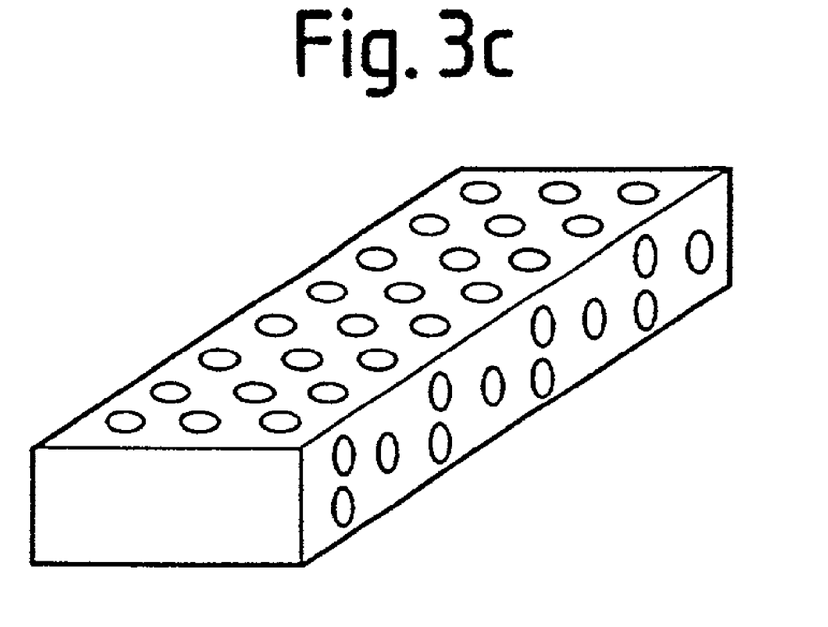

4. Particular implants made from the material according to the invention, which are employed in specific fields of use, can be produced in large numbers in standardised size gradations from blanks by, for example, chip-r moving methods. A number of advantageous embodiments are shown in FIG. 3a–c. For xample, FIG. 3a shows a so-called alveolar augmentation article for filling an alveolus after extraction of a tooth;

FIG. 3b shows a conical disc which serves for closure of a trephination opening in the cranium; FIG. 3c shows an advantageous embodiment of a flat augmentation article for filling out or raising an atrophied jaw ridge, a so-called sinus lift.

5. 2 mol of calcium hydrogen phosphate and 1 mol of calcium carbonate in powder form were mixed, compressed to make a formed element, transferred to a ceramic crucible and sintered for 24 hours at 1100° C. The sintered element was broken up and ground; 1% of an unreacted powder mixture of the formulation given above was added thereto and intimately mixed therewith. The mixture was then compressed to make a formed element and again sintered for 24 hours at 1100° C. After cooling, the sintered element obtained was mechanically processed and brought into a form according to FIG. 2e. The formed piece was finally baked again for 24 hours at 950° C.

6. Experimental Results

Figure 4A:
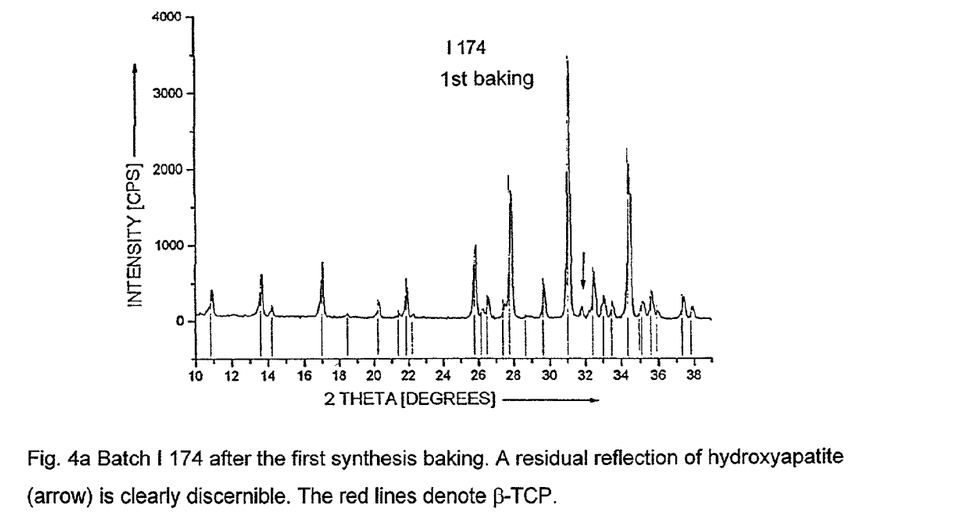
FIG. 4a is a graph of intensity (CPS) versus 2 Theta (degrees) of an X-ray recording of an exemplary material after a first (CPS) sinter bake.
Figure 4B:
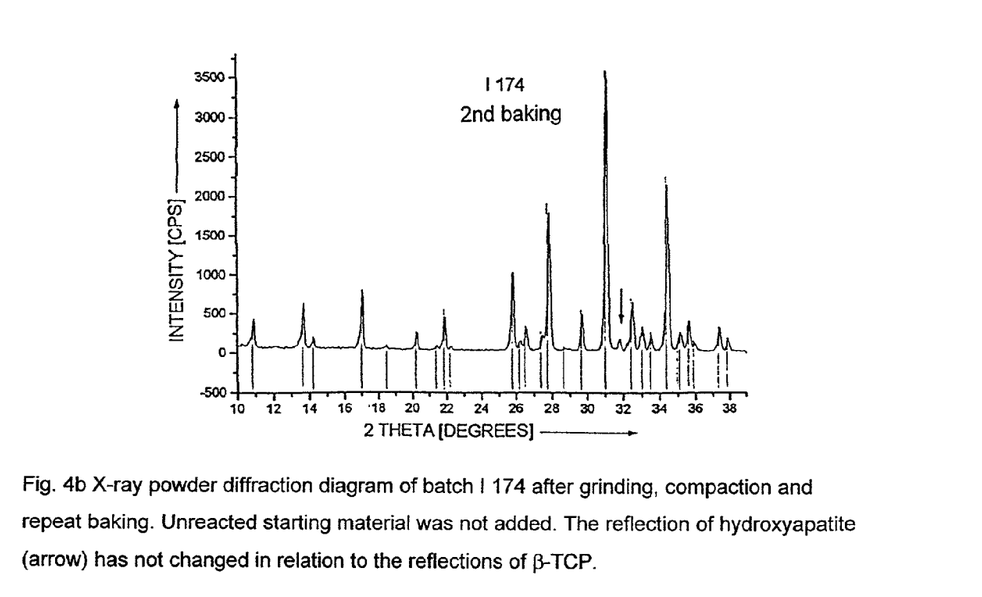
FIG. 4b is a graph of intensity (CPS) versus 2 Theta (degrees) of the material shown in FIG. 4a after further processing and a second sinter bake.

The successful development step for achieving phase-pure β-TCP ceramics is documented by two X-ray recordings (FIG. 4a, 4b). FIG. 4a shows the material after the first sinter bake. Still clearly discernible Is a residual reflection of hydroxyapatite (arrow). After a first sinter bake, the batch was broken up again, homogenised and compacted again. No unreacted starting material was added to the material. The X-ray powder diffraction diagram still shows a residual reflection of hydroxyapatite after that second sinter bake.

Figure 5A:
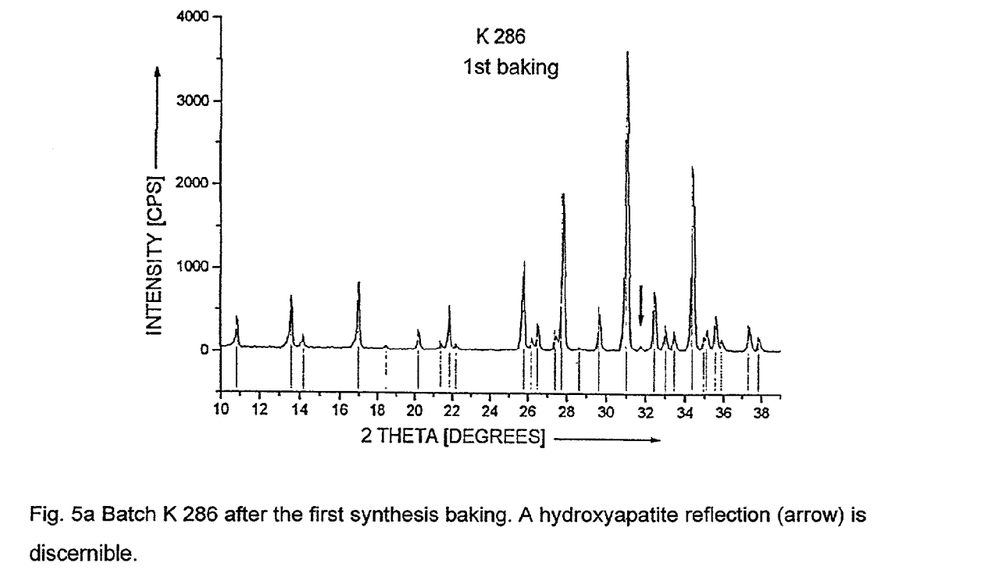
FIG. 5a is a graph of intensity (CPS) versus 2 Theta (degrees) of an X-ray of a different material batch after a first baking.
Figure 5B:
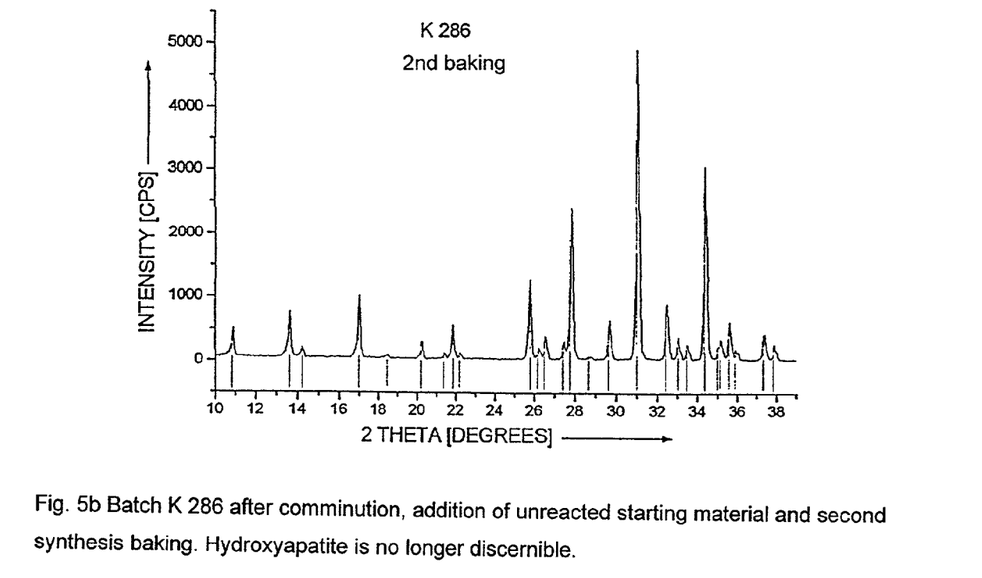
FIG. 5b is a graph of intensity (CPS) versus 2 Theta (degrees) of the material shown in FIG. 5a after further processing and a second sinter bake.

Using a second example, it may be demonstrated that the hydroxyapatite foreign phase is, surprisingly, no longer discernible as a result of the addition of unreacted starting material to a batch of β-TCP baked once. After the first sinter bake, the batch K 286 clearly shows a HA reflection at about 31.7° 2θ. After again powdering the pre-synthesised material and mixing with unreacted phosphate powder, the resulting material was also subjected to a second sinter bake. In FIG. 5b, an HA reflection is no longer discernible.

It is accordingly possible here to demonstrate impressively that the formation of HA is completely suppressed as a result of dissolution thereof in the melt after unreacted material is added, with, at the same time, seed formation being facilitated by the β-TCP already present.

The invention claimed is:

1. Resorbable bone replacement and bone formation material based on porous β-tricalcium phosphate (β-TCP), produced by
   (a) baking a phosphate powder of a chemical composition having residue on baking which yields theoretically chemically pure tricalcium phosphate;
   (b) forming blanks having microporosity using the chemically pure tricalcium phosphate (β-TCP); and
   (c) providing the baked blanks with substantially tubular pores, wherein
formation of thermodynamically stable adjacent phases of β-TCP is inhibited, wherein the method further comprises;
   (i) powdering a presynthesis product obtained according to step (a),
   (ii) optionally baking the powdered presynthesis product together with phosphate powder according to step (a) and powdering the material obtained and optionally repeating step (ii) at least once;
   (iii) compressing the powdered product obtained in step (i) or step (ii) to form the blanks of step (b) and subjecting the blanks formed to final ceramic baking; and
   (iv) subjecting the baked blanks, at least about 99.5% of which consists of pure β-tricalcium phosphate (β-TCP), to step (c), wherein the baked blanks are resorbable in vivo.

2. Formation material according to claim 1, wherein the formation material has chemical and crystalline purity, a structure, microporosity and macroporosity that make possible rapid, foreign-body-reaction-free, biochemically orientated integration and resorption in bone.

3. Resorbable bone replacement and bone formation material, produced by
   (i) baking phosphate powder of a chemical composition having a residue on baking which yields theoretically chemically pure tricalcium phosphate as a presynthesis product, and powdering that presynthesis product;
   (ii) baking the powdered presynthesis product and powdering the material obtained and optionally repeating step (ii) at least once;
   (iii) compressing the powdered product obtained in step (ii) to form shaped blanks of resorbable β-tricalcium phosphate (β-TCP) having microporosity and subjecting the blanks formed to ceramic baking; and
   (iv) providing the compressed baked blanks with substantially tubular macropores.

4. Formation material according to claim 1, obtainable by baking at a temperature below 1200° C. in the β-tricalcium phosphate (β-TCP) phase region.

5. Formation material according to claim 1, obtainable by using in step (ii) and/or step (iii) from 1 to 50% by weight, especially from 1 to 25% by weight, phosphate powder, the weight based on the total weight of phosphate powder and already baked material.

6. Formation according to claim 1, wherein the baked β-tricalcium phosphate (β-TCP) comprises sintered primary particles, wherein the blanks have a generally uniform sintered structure with interconnected microporosity having pore widths in the region of from about 2 μm to 15 μm and/or a matrix of the β-tricalcium phosphate (β-TCP) primary particles that is tightly sintered to microporosity, especially with microparticles that are loosely bound in the sintered structure and/or phagocytosable, having a diameter of max. 15 μm, being absent.

7. Formation material according to claim 1, wherein the baked blanks comprise a microporosity of at least about 20% by volume, based on the overall porosity, the overall porosity defined by micro- and macro-porosity.

8. Formation material according to claim 1, wherein the compressing step comprises providing the compressed blank with tubular pores with the aid of a compression mould of optionally more than one part.

9. Formation material according to claim 1, wherein the providing the baked blanks with substantially tubular pores comprises providing the baked blank with the substantially tubular pores by milling and/or drilling.

10. Formation material according to claim 1, wherein the blanks are in block form having a block surface, with 2- or 3-dimensionally oriented macroscopic substantially tubular pores passing through each block, which are in each case arranged substantially perpendicular to the block surface and/or to an imaginary plane laid through the block or against the block and form an interconnecting system of the tubular pores.

11. Formation material according to claim 10, wherein a block intended for implantation, together with its substantially tubular pores, can be so oriented for implantation or on processing prior to implantation so that at least one direction of orientation of the tubular pores corresponds to a biomechanically or biofunctionally intended direction of growth.

12. Formation material according to claim 1, wherein the tubular pores have radii in the region of from about 100 μm to about 2000 μm.

13. Formation material according to claim 1, wherein the blanks are in block form, each block comprising tubular pores that are spaced apart at a defined spacing with respect to one another, the spacing corresponds to a wall thickness of less than about 4000 μm.

14. Formation material according to claim 1, wherein the blanks have an overall porosity, defined by micro- and macro-porosity, of more than about 50% by volume.

15. Formation material according to claim 1, wherein the blanks with the substantially tubular pores have a macroporosity of from 25 to 50% by volume, and especially from 30 to 40% by volume, based on the overall porosity defined by micro- and macro-porosity.

16. Formation material according to claim 1, wherein the blanks have a block form that is a simple geometric shape.

17. Formation material according to claim 1, wherein the blanks define a semi-finished product, configured to allow subsequent mechanical processing and/or for individual adaptation in the case of bone defect in mouth or jaw medicine, orthopaedic surgery or trauma surgery.

18. Formation material according to claim 11, wherein the blank material is compressed, baked and/or sintered, only to a degree such that it can be processed using medical or dentistry tools available to a practitioner.

19. Formation material according to claim 11, wherein the block has been brought into the form of an individual prosthesis with the aid of a medical CAD/CAM method.

20. Formation material according to claim 16, wherein the simple geometric shape is generally one of a cube, a tapered body, a rectangular box-like body, a wedge, a cone, a cylinder or a disc.

21. Formation material according to claim 1, wherein the substantially tubular macropores have substantially uniformly sized diameters, and wherein some of the tubular macropores are arranged in the shaped body to cross through other of the tubular macropores.

22. Formation material according to claim 3, wherein the substantially tubular macropores have substantially uniformly sized diameters, and wherein some of the tubular macropores are arranged in the shaped body to cross through other of the tubular macropores.

23. Resorbable bone formation material produced by:
pressing a baked body of sintered β-tricalcium phosphate (β-TCP) into a blank body of resorbable bone formation material having micropores;
shaping the blank body into a desired shape; and
inserting macropores having a substantially constant width over at least a major portion of a length thereof into the shaped body, the micropores extending through the shaped body in at least two different dimensions whereby some of the micropores cross over other of the macropores and also micropores.

24. Formation material according to claim 23, wherein the inserting comprises drilling.

25. Formation material according to claim 24, wherein the micropores are substantially tubular and wherein the micropores are interconnecting micropores.

26. Formation material according to claim 25, wherein the macropores have a substantially common uniform diameter.

27. Formation material according to claim 25, wherein the macropores are arranged as groups of substantially parallel macropores that extend through the body in three dimensions.

28. Formation material according to claim 23, wherein the shaping is carried out by milling the blank body into the desired shape.

* * * * *

UNITED STATES PATENT AND TRADEMARK OFFICE
CERTIFICATE OF CORRECTION

PATENT NO. : 7,087,540 B2 Page 1 of 1
APPLICATION NO. : 10/085526
DATED : August 8, 2006
INVENTOR(S) : Heide et al.

It is certified that error appears in the above-identified patent and that said Letters Patent is hereby corrected as shown below:

Column 9,
Lines 64-65 should read -- (b) forming blanks having microporosity using the baked β-tricalcium phosphate (β-TCP); and --

Column 10,
Lines 2-4 should read -- the β-tricalcium phosphate (β-TCP) is baked at least twice and the formation of the thermodynamically stable adjacent phases of β-TCP is inhibited, wherein the method further comprises; --

Signed and Sealed this

Twelfth Day of December, 2006

JON W. DUDAS
*Director of the United States Patent and Trademark Office*